United States Patent [19]

Nosek

[11] Patent Number: 5,031,642

[45] Date of Patent: Jul. 16, 1991

[54] INTEGRATOR - COLLECTOR FOR SURGICAL/MEDICAL PROCEDURES

[76] Inventor: Bettie L. Nosek, 10044 Adams Ave. #205, Huntington Beach, Calif. 92646

[21] Appl. No.: 334,297

[22] Filed: Apr. 6, 1989

[51] Int. Cl.⁵ .............................................. A61N 1/00
[52] U.S. Cl. .................... 128/906; 604/317; 604/322
[58] Field of Search .................. 604/317, 66, 67, 322, 604/318, 356; 128/630, 696, 906, 620, 695, 638, 773; 40/310

[56] References Cited

U.S. PATENT DOCUMENTS

| | | | |
|---|---|---|---|
| 3,146,944 | 9/1964 | Grippi, Jr. | 604/317 |
| 3,199,507 | 8/1965 | Kamm | 604/356 |
| 3,575,225 | 4/1971 | Muheim | 604/356 |
| 3,618,836 | 11/1971 | Bushnell | 40/310 |
| 4,008,802 | 2/1977 | Freitag | 206/63.3 |
| 4,029,097 | 6/1977 | LeRoy | 604/356 |
| 4,295,537 | 10/1981 | McAvinn et al. | 177/15 |
| 4,402,373 | 9/1983 | Comeau | 128/771 |
| 4,422,548 | 12/1983 | Chessman et al. | 206/370 |
| 4,589,372 | 5/1986 | Smith | 604/66 |
| 4,593,702 | 6/1986 | Kepski et al. | 128/696 |
| 4,637,513 | 1/1987 | Eldrige, Jr. | 206/370 |
| 4,705,048 | 11/1987 | Pfohl | 128/773 |
| 4,716,904 | 1/1988 | Meno | 128/695 |

*Primary Examiner*—Francis Jaworski
*Assistant Examiner*—George Manuel
*Attorney, Agent, or Firm*—Barry A. Bisson

[57] ABSTRACT

An integrator-collector contains a time-corellated digital receiver for measuring, displaying, and recording fluid loss (including blood) from surgery or crisis procedures and for maintaining, displaying, and recording a count of secured surgical items such, as needles and sponges. The integrator-calculator computes total blood loss during surgery by means of an electronic beam, which upon activation by a surgical sponge, triggers the automatic conversion of the weight of the sponge into cubic centimeters of blood loss.

Fluid balance can be computed and reported from a corellation between blood lost, and loss from other fluids, such as vomitus and urine, and plasma intake and the intake of other fluids, such as clear intravenous fluids.

13 Claims, 2 Drawing Sheets

INTEGRATOR - COLLECTOR FOR SURGICAL/MEDICAL PROCEDURES

CROSS-REFERENCE TO A RELATED APPLICATION

This application is a continuation-in-part of U.S. Ser. No. 003,783, filed Jan. 15, 1987, and now abandoned in favor of the present application. The entire disclosure of said U.S. Ser. No. 003,783, as filed, is hereby incorporated herein by this reference.

The purposes of the invention include:
1. Count sponges, needles, and other secured surgical items.
2. Tabulate and display current blood and fluid loss.
3. Display current totals.
4. Provide a tangible form such as a printed copy, computer disk, or video tape of the operating or other hospital transactions.
5. Provide fluid balance status of a patient throughout the surgical procedure and the immediate postoperative period.
6. Provide a computer program to display surgical protocol by means of a floppy disk and video terminal.
7. Provide activation of video camera which will make a permanent audio and visual record of operating room transactions.
8. Provide patients' identification information for each procedure.

BACKGROUND OF THE INVENTION

1. The Field of the Invention

The present invention is in the field of medical electronics, and more specifically relates to an intelligent computer calculator for collecting, displaying, and recording data that relates to a patient's fluid balance during surgery, and to the status of secured surgical items used during surgery, such as sponges and needles. The computer calculator not only records and displays the number of sponges utilized in the patient during surgery, but it can also translate the weight of sponges into fluid volume lost by a patient, and it can provide a manual mode by which additional fluid loss through abdominal, chest, or bladder drainage may be added to blood loss to obtain an accurate estimate of the entire fluid loss of a patient during a procedure. Because it is standard practice in an operating room to count sponges during surgery, the computer calculator can also automatically count, display, and a record sponges as they are discarded from the patient. Other secured items such as needles may also be manually calculated, displayed, and recorded on the computer in single, multiple or predetermined multiple suture packages. The computer can provide an audible tone to inform the operating room associates of excessive fluid loss, and it can provide a printed or other tangible copy of each transaction involving fluid loss, sponges, needles, and other secured items monitored by the invention.

2. The Prior Art

In U.S. Pat. No. 4,295,537 filed Oct. 20, 1981, for Sponge Measuring Device by McAvinn et al., there is described a device that attempts to weigh and count surgical sponges. The device provides a receptacle for placement of the sponges and a housing device for collection of the sponges to facilitate the sponge count at the end of the procedure. The device is designed to allow the operator to weigh the plurality of collected sponges and to subtract the weight of any equal number of dry sponges to estimate the amount of blood loss in the wetted, discarded sponges.

A counting and weight collector for surgical sponges was also described in U.S. Pat. No. 3,367,431 filed Feb. 6, 1968 by Dorothy H. Prindle Baker for Surgical Sponge Collector with Means for counting and Weighing Sponges. The device provided a cabinet with receiver slot, a counter on the cabinet, a light source in the cabinet projecting a beam across the slot, and a light-responsive device that activated the counter when a sponge passed through the slot. The invention provided a continuous and visible indication of the number of sponges and the total weight.

In the U.S. Pat. No. 4,422,548 filed Dec. 27, 1983 for sponge measuring device by Cheesman et al., there is described a device for counting, weighing, and disposing of soiled surgical sponges. The device provides a receptacle for placement of the sponges, a housing device for collection of sponges, and a scale for weighing the sponges. The device is designed primarily to provide a system for counting, weighing, and disposing of soiled surgical sponges with a minimum of handling by operating room personnel.

The device of Cheesman et al., it provides only the weight of soiled sponges. It is more practical and accurate to utilize the invention which includes a device that provides a means for electronically converting the weight of the soiled sponge into volume of blood contained in the soiled sponge. This is more accurate and practical because volume of blood loss is the determining factor for replacement of blood or fluid to the patient. The Cheesman et al., device does not convert the weight of the sponge into volume of cubic centimeters of blood loss.

Urine, like blood, is also a volumetric fluid loss, and is more accurately accounted for when the loss is measured volumetrically, in cubic centimeters rather than in grams of weight. The Cheesman et al. device provides no capability for electronic conversion of urine weight or blood weight into parameters, and one of ordinary skill in the art is accustomed to dealing with volumetric, cubic centimeter parameters.

The device described by Cheesman et al., also fails to provide the capability to manage information about fluids other than blood, which are of significance during an operating procedure. The capability to enter information about the addition of fluids to the patient, and the deletion of fluids from the patient, is central to the capability of maintaining an accurate electronic assessment of a patient's fluid balance status. The significance and importance of maintaining a current assessment of the patient's fluid balance during a procedure is obvious to anyone of ordinary skill in the art.

U.S. Pat. No. 3,618,836 of Bushnell, et al., there is described a device for encoding containers containing biological samples.

While the Bushnell, et al., device provides a needed service for biological samples handling, it is inadequate and ill-equipped to provide the comprehensive management of data, as provided by the present invention.

The Bushnell, et al., device provides no capability for fluid balance assessment, no capability for soiled sponge handling after recording and counting them, and no capability for a surgeon to obtain electronic data from a floppy disk facility, such as can be provided in the device in the present invention.

The types of collectors-counters demonstrated in the prior art, do not provide the automatic translation of sponge weight into cubic centimeter or mililiters of blood loss. The former devices also make no provision for the addition of other fluids frequently loss during routine surgeries; all such lost fluids must be taken into consideration before blood or fluid replacement therapies are instituted by the physician. The devices also provide no indication of alarm to alert operating room associates of the excessive nature of blood loss nor do the devices provide manual access to the addition of other secured surgical items such as smaller needles or sponges, nor do the other devices provide fluid balance status. The prior art also provides no printer or other tangible record of transactions during surgery for entry in the permanent record on the patient's chart.

SUMMARY OF THE INVENTION

The present invention is an intelligent integrator-collector that provides a current and total fluid loss and intake status of the patient at all times during surgery. The invention also can provide a current and total accounting of surgically secured items, such as sponges, needles, and instruments which will enable the operator to account for such items with greater accuracy and consistency by reducing chance for human error through electronic computation of sponges, needles, and instruments.

The margin of error will be further reduced by the computer because it will enable the sterile nurse to utilize the record to cross-check the number of needles on the sterile field with the total displayed on the terminal at any given time during surgery.

The computer also can greatly reduce the margin of error in the estimation of blood/fluid loss from the patient during surgery because it provides an electronic means for automatically translating the weight of a used, discarded sponge into the approximate amount of fluid loss. Compared with the previous routine method of estimating blood loss in which the physician estimates blood loss by visually approximating the amount of blood in a sponge.

Because the viscosity of a patient's fluid varies from patient to patient, and because the absorptive rate varies among different sponge manufacturers or from laundering routines for those non-disposable sponges, it is increasingly important to improve the method of estimating blood loss by means of available electronic technology.

DETAILED DESCRIPTION OF THE PREFERRED EMBODIMENT

Figure 1:
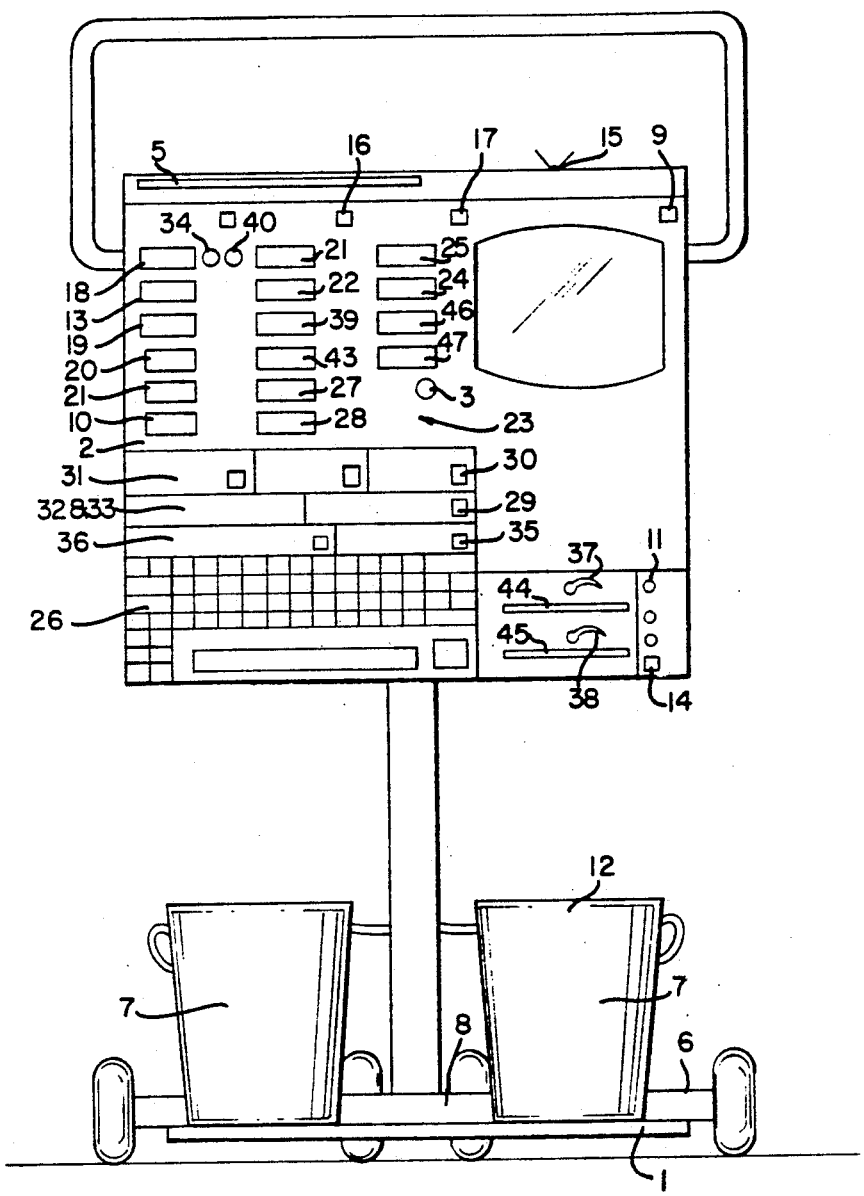
FIG. 1 Full frontal perspective of a preferred embodiment.
Figure 2:
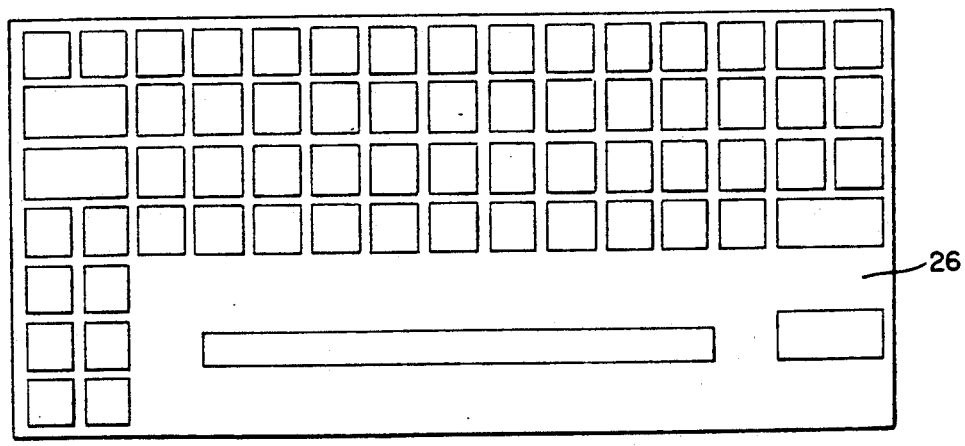
FIG. 2 Close-up of front perspective of the embodiment in FIG. 1.
Figure 3:
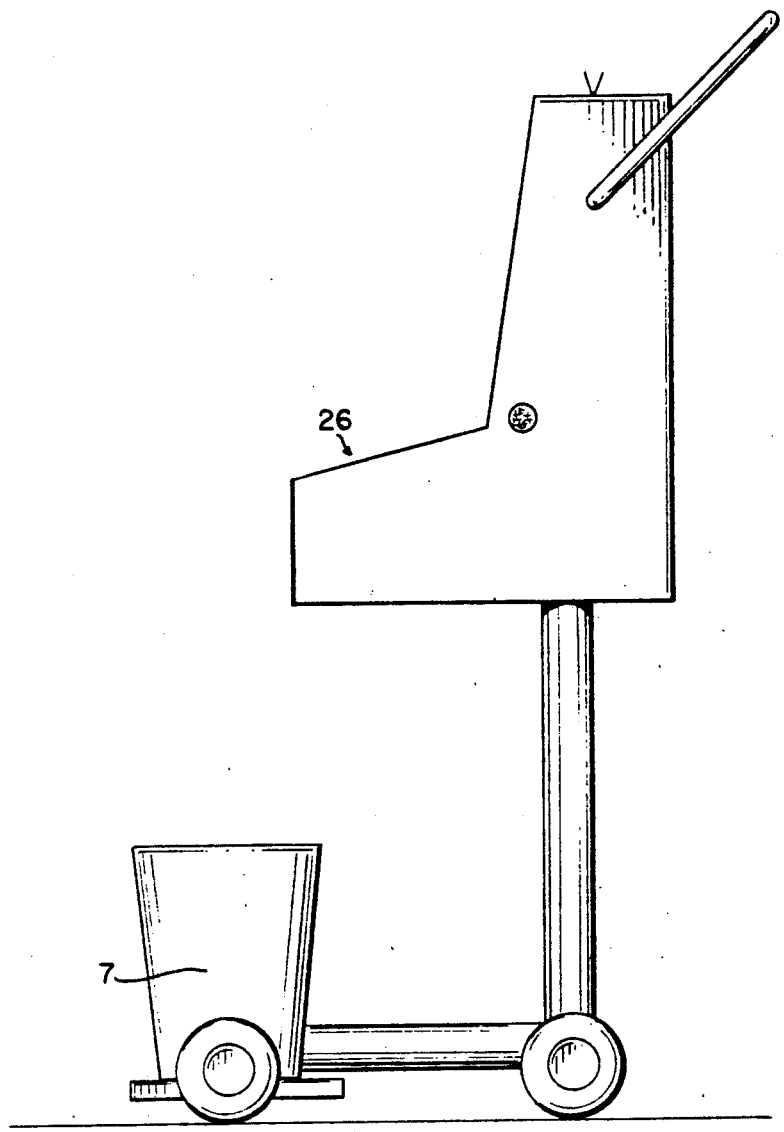
FIG. 3 Side view of the embodiment in FIG. 1 with housing.

Referring now to the drawings, FIG. 1 is a perspective view of the external features of the preferred embodiment of the present invention, which comprises a sponge weighing means 1, a sponge counting means 18, a needle counting means 13, a display terminal 4, a printer for recording each transaction 5, and a support assembly that facilitates movement about the operating room 6. The weight measuring means may be of any suitable types, such as the device disclosed in U.S. Pat. No. 4,295,537 incorporated herein by reference. As shown in FIG. 1, the weight measuring means 1, has a plurality of leads extending internally from the sponge receptacle 7 to the calculating device 8, to carry the signal indicating weight load and to automatically translate the weight into volume 23 of fluid lost and display on terminal 4.

With reference to FIG. 1, the sponge counting means 12, may be of any suitable type such as the light beams photocell, and solenoid described in U.S. Pat. No. 3,367,431, incorporated herein by reference. The particular construction of the solenoid, photocell, and counter do not form a part of this invention. The sponge receptacle is equipped with a manual mode that permits entry into the receptacle for retrieval of discarded sponges without interfering with the total of accumulated sponges and without triggering the photocell. Once the sponges have been removed from the receptacle, the operator may resume the automatic mode that automatically counts each sponge as it breaks the light beam 12 and translates the sponge weight into volume of fluid lost by the patient. The signal will comply with the standard procedure that sponges should be removed in increments of five (5).

The display terminal of the counting and weighing means FIG. 1 displays 4, the concurrent total number of sponges collected throughout the duration of the procedure along with the current number of sponge in the receptacle, 7. The estimated blood loss which is derived from the weight of the sponges and automatically translated and displayed as volume of fluid loss is displayed on the terminal 4. These readouts enable the operating room or other medical associates to determine the total amount of blood lost 21,22, the total fluid lost from urine 39, total lost from emesis 43, total lost from cavity 27, and total lost from other sources 28. The readouts also display the total number of sponges 18 that have been used and discarded during the entire procedure. The manual mode of operation 10 which enables the operator to remove sponges or debris from the receptacle 7, and be activated with view of the total number of used sponges and the total fluid loss 29. Another push of the button 10, reverts the computer to the mode in which the sponges are counted, weighed, and the weight is automatically translated into volume lost and displayed 4.

This invention is simple to operate with all the controls conveniently mounted on the compact front control panel within easy reach and visibility of the operation, FIG. 1. The on/off pushswitches, 11, lights when depressed so the operating mode can be readily identified. The mechanism contains an internal clock that automatically enters the time of each transaction onto the printed record 5 for easy reconstruction of times events during the procedure. The time of the initial entry, each subsequent entry, and the final count are entered automatically onto the printed record without requiring a manual input by the operator. The present invention also contains an internal calendar that provides each printed record with the appropriate date automatically without requiring the operator to manually input the date on a daily basis or to manually instruct the computer to include the date.

The present invention also provides highly visible data and updated displays in the front terminal pattern, FIG. 1. These are reflected on a video terminal 4 in large numbers that can be easily be seen from various reference points in the room so that all interested and responsible members of the surgical team can have visible access to a patient's fluid balance status 29 and to the surgical count 32,33. Changes in the numbers on the display and additions to the sponge receptacle are also monitored by an audible signal 15 that alerts members that change in the display module has occurred. A different modulation of the signal serves as an alert to operating members that the patient has undergone extensive blood 21,22 loss with parameters that may be established by the surgeon or other responsible party and may be manually introduced on the control panel 23 by the operator. Parameter changes during the procedure may be changed while the computer 23 is in the manual mode. As shown 13 in FIG. 1, the needle counter portion can be operated similarly to a computer-calculator in that the addition of the needles are programmed into the computer by pressing the key 13.

To gain access to the needle mode of the computer, the 13 key is depressed before any additions, deletions, or changes are made. The depression of 13 automatically places the computer to the needle counting mode and the 13 designation is easily visible on the digital readout for needles. Needles may be added manually at the keyboard 26, or by magnetic touch on pad located on a sterile table and transmitted by radio signal to the computer 9. The needle counter portion of this invention maintains a current total of all needles that have been used in the process. It provides an automatic readout of the numbers of needles at any given time which enables the sterile or non-sterile nurse to check the totals of needles in the field of surgery as compared with the computers calculated total of needles 31. This feature is an important one because frequently the sterile and non-sterile nurse are too busy to take prelimary counts that might warn them early of a needle discrepancy. Computer calculator allows either nurse to be informed of the total count of needles and to therefore make preliminary checks of the needle count.

To access the sponge portion of the calculator counter, a sponge key 18, is depressed and followed by additions, deletions, etc. Similar transactions can also be made for instruments by depressing the instrument key 19, cottonoids by depressing the key 20, peanuts by depressing key 21, and so forth, followed by additions, etc.

The scope of the present device can also cover other surgically secured items such as instrument counts. This feature can also be available in an independent module for those facilities that routinely count instruments during surgical procedures. The device can also be used to count other surgical secured items such as small dissecting sponges called lobectomy sponges or peanuts, or 4×4 sponges, neurosurgical sponges called cottonoids, and other specialty items such as rubber boots used in cardiovascular surgery, connectors pacing wires, probes, and other items that may be inadvertently left in a patient prior to the closing procedure.

Because it has a computer interface 14, the device can also be capable of displaying blood or fluid loss from another room. A surgeon with consecutive operative procedures may desire to have the loss displayed from a serious patient in the recovery room, and this device would allow the display of more than one patient simultaneously even though the patients are not in the same rom, or even on the same floor of the hospital.

Within the scope of this device, can be the capability to interface with a physician's personal office computer 14 following surgery to provide the physician a current total of blood loss while the patient is in the hospital and the physician is in the office.

The scope of the present device can also be capable of determining output 16, intake 17, and fluid balance 29 of the patient. On the face of the device, in FIG. 1, the intake section, 17, can be used to measure patient intake by depressing the key appropriate to intake 17. For example, blood replacement for the patient can be added by depressing the blood key 24, and following it with addition on the keyboard, 26. Clear fluids such as intravenous dextrose and water can be added by pressing the clear key 25, and following with an addition on the keyboard 26. Similarly, the plasma key 46 registers plasma, and the other key 47 registers fluid intake not labeled on the computer face. The computer registers this information as intake and holds it in memory or displays in on the terminal 4.

In the output section, the sponge key 21 automatically reflects the volume of cc's (cubic centimeters) lost in sponges, while the suction key 22, after being depressed, requires a manual input on the keyboard 26 of the number of cc's present in the suction bottle.

The emesis key, 43, cavity 27, and other 28, keys also require manual keyboard entry to record the amount of lost fluid. The cumulative total, however, is automatically tabulated and maintained in computer memory as output, which can be retrieved by pressing the output key 16. The total intake is retrieved and displayed by pressing intake key 30.

To obtain an accurate estimate of fluid balance, the balance key, 29, can be depressed to reflect the positive or negative position of the patient in regard to fluid balance. To obtain a proper count of surgical secured articles, the count key 31, can be depressed followed the needle key 13, and it will give the total count of needles on the terminal 4. To access count on sponges, the sponge key 18 must be depressed followed by the total count key 31. The correct key 32 will light to indicate the correct amount, and the incorrect key 33 will light to indicate incorrect count.

A print-out of the entire operating or other hospital related incidents can be recorded by pressing the print key, 35, to active the printer 5. To access the medical library menu, the menu key 36, can be depressed and a menu will appear on the screen 4. The menu selection can be called on the keyboard 26, and the selection of the proper floppy disk can be read on the screen. Once the floppy disk is obtained, it can be inserted into either receptacle 44,45, and activated by fastening latches 37,38. The disk can then reflect surgical procedure, protocol, drugs of choice, postoperative care recommendations or whatever material is desired.

To obtain urine measurements, simply press the urine key 39, and place the urine bag in the receptacle 7, and the weight will be measured by the means of a scale, FIG. 1, 40, and will be automatically registered in the computer calculator, or the volume can be entered manually on the keyboard, 26, after depressing the urine key 39.

The embodiments of the invention include an integrator-collector apparatus for use in medical-surgical procedures with the apparatus comprising the combination of a means of counting surgical sponges prepared for potential use in an operating procedure by the breaking of a surgical sterile seal, a measuring means for estimating the amount of blood absorbed by the surgical sponges actually used in the patient, a measuring means for estimating blood removed by suction from a patient during an operating room procedure, a means for providing an estimate of incremental blood loss during the surgical procedure and the total blood loss at the termination of the procedure, with the means for providing this estimate being operatively associated with the measuring means.

Figure 4:
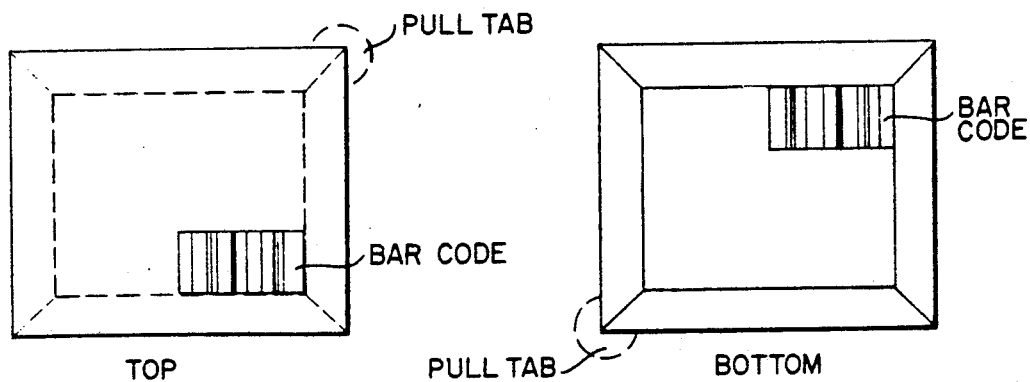
FIG. 4 Top and bottom view of packaging of sterile sponges and indicia.

This invention further includes a means for counting the surgical articles prepared for potential use in the operating room procedure by the breaking of a surgical seal. This invention also consists of external packaging indicia FIG. 4 on surgical sponges as a means of providing and interpreting a numerical item of the items bearing the indicia. The invention is an integral part of the indicia and surgical seal. This invention also consists of indicia or external packaging on sponges and needles, and the interpretation of this indicia provides a record of the surgical articles as well as a record of personnel performance. The invention and indicia are an integral part of the surgical seal. The packaged surgical sponge contains a surgical sterile seal closing an outer surgical wrapping which describes inner contents, and which can be interpreted by electronic, optical, or mechanical means. The sponge in the invention with indicia indicate the number of sponges in the package, the sponge size, absorbency factor, weight, and the presence of an x-ray opaque indicator.

The invention can also provide the means to determine the amount of urine lost by the patient during the procedure and/or during acute periods following the procedure. The invention's ability to measure urine loss comprises a measurement of volume or weight of urine in the collection bag.

The invention also can comprise a means of reporting electrocardiogram (ECG) patterns 34 of the patient during surgery. This invention provides a connection to the ECG patterns by establishing a connection to the apparatus measuring the patient's ECG pattern. The invention receives ECG patterns from leads attached to the patient in an unsterile area and projects these patterns onto an oscilloscope in a unsterile area.

This invention can also provide a means for counting needles comprising a magnetic touch pad in the sterile area and the means for measuring impulses caused by the needles impinging on said pad in sterile areas, and transmitting the needle touch to the apparatus 40 for purposes of counting and tracking needles used during the procedure. This invention provides magnetic needle tracking for translation by means of a radio transmitter signal or a cable connector to the apparatus 40.

The invention also can provide a means for measuring the hematocrit percentage of the patient while simultaneously measuring the hematocrit irrigation fluid remnants, and it can use the patient's venous hematocrit as the standard; whereby the fluid balance can be maintained by accurate estimate of blood loss through the irrigation.

The invention can also provide an integrator function by means of comprising a printing mechanism adapted to print on continuous paper strip, with the printer being activated by the well-known means of impulse generation from the apparatus, with the impulses causing the printing of a continuous count of surgical sponges, a continuous estimate of incremental blood loss, and a count of surgical articles during the procedures. This invention will also record date and time of every instrument, sponge, needles surgical articles, as well as output and intake and at the same time, will label the patient's record with name, surgeon identification. number, operating room number, room number, procedure type, specimen taken, fluid balance status and whether or not the counts are correct 5.

The invention can also provide a means for corellating each material used in the operation with a billing price to the patient, whereby said apparatus can generate a record which can be used for billing and reordering purposes. The invention can also provide a means for reporting and recording surgical specimens taken during the course of an operation. It can also provide labels for specimens 5.

Within the scope of this invention is a process of inventory control including recording, charging, and reordering items such as nondisposable surgical items implanted or used during the procedure. For example, a hip nail, which can be implanted after being sterilized and used to repair a fractured hip. After the implant is sterilized, it is removed from sterilizer by the scrub nurse, and at the points where it is implanted, the scrub nurse can relay pertinent information such as nail size, type and number of screws to the circulating nurse for appropriate charging and reordering through the apparatus keyboard 26. Another function of the apparatus is quality control through the performance review and cost containment, which can be monitored by using the real-time clock and the indicia-bearing sterile items to monitor an employee's progress during the preoperative period used to prepare the room for procedures.

The inventions's scope also includes a means for providing information to the operating surgeon relating to procedure or protocols through a medical library 36 floppy disk entry viewed on the computer terminal. This invention can provide the means for giving information to the surgeon relating to operating procedures on computer programs containing requisite information in combination with means for assessment desired information and means for reporting information through the apparatus floppy disk drive 44, 45.

For example, the apparatus can be connected to an external library such as disk, comprising a computer program relating to surgical procedures being performed or anticipated during the operation. At any stage of the procedure, the surgeon could request the operator to access a given computer program relating to a particular procedure. Alternately the computer programs anticipated for particular procedures could be assessed within the apparatus. Similarly, programs for billing, inventory, cost containment, and performance review could be contained within the apparatus or within an external library.

In one embodiment, all operating rooms are electronically connected with an equal number of computer terminals in a library, and during the course of the operation, library personnel could be requested to provide information or protocol to surgical personnel during the procedure. The recording apparatus could also be used to record any pertinent information gathered during the procedure.

Within the scope of the invention is also a means to record visual images and attendant sounds of the operating room process, and can also be connected to similar means in other areas of the hospital to provide a record in tangible form of all procedures or crisis emergency situations.

FIG. 5 presents top and bottom views of the packaging of sterile sponges (or other surgical articles) wherein the surgical seal comprises a peel tab containing a bar code (or other indicia); said peel tab can be used to input information on the bar code into the integrator-collector.

What is claimed is:

1. An integrator-collector apparatus for use in operating room procedures wherein blood from a patient is absorbed by surgical sponges, said apparatus comprising, in combination:
   a) a means for counting surgical sponges which are prepared for use in an operating room procedure said patient by the breaking of surgical sterile seals;
   b) a measuring means responsive to said means for counting for estimating the amount of blood absorbed by the surgical sponges actually used in said patient during said procedures;
   c) a measuring means for estimating blood removed by suction from a patient during said operating room procedure;
   d) a means for providing an estimate of incremental blood less during said operating room procedure and for providing an estimate of the total blood loss at the termination of the procedure, said means for providing said estimates of blood loss being operatively associated with each of said measuring means defined in parts (b) and (c), above;
   e) a means for reporting and recording surgical specimens taken during the course of said operating room procedures and,
   f) a means for providing labels for each of said specimens.

2. The apparatus of claim 1 wherein said counting means comprises indicia on external packaging on said surgical sponges and means for interpretation of said indicia to provide a numerical record of surgical articles and sponges bearing indicia.

3. The apparatus of claim 2 wherein said indicia are an integral part of said surgical seal.

4. The apparatus of claim 1 further comprising means for providing information to an operating surgeon relating to operating procedures or protocols.

5. An integrator-collector apparatus for use in operating room procedures wherein blood from a patient is absorbed by surgical sponges, said apparatus comprising, in combination:
   a) a means for counting surgical sponges which are prepared for use in an operating room procedure on said patient by the breaking of surgical sterile seals;
   b) a measuring means responsive to said means for country for estimating the amount of blood absorbed by the surgical sponges actually used in a patient during said procedure;
   c) a measuring means for estimating blood removed by suction from said patient during said operating room procedure;
   d) a means for providing an estimate of incremental blood loss during said operating room procedure and for providing an estimate of the total blood loss at the termination of the procedure, said means for providing said estimates of blood loss being operatively associated with each of said measuring means defined in parts (b) and (c) above; and
   e) a means for measuring hematocrit percentage of said patient while simultaneously measuring hematocrit of irrigation fluid remnants, using said patient's venous hematocrit as a standard; whereby fluid balance can be maintained by accurate estimates of blood loss through irrigation.

6. The apparatus of claim 5 further comprises means to determine urine loss from said patient during the procedure and/or during acute periods following the procedure.

7. The apparatus of claim 6 wherein said means to determine said urine loss means for measurement of volume or weight of urine in a collection bag.

8. The apparatus of claim 6 wherein said means of measuring said urine loss means for measurement of volume and weight of urine in a collection bag.

9. The apparatus of claim 5 and adapted to count surgical articles comprising a ferrous metal wherein said means for counting comprise a magnetic touch pad and a means for monitoring impulses caused by said articles touching said pad and means for transmitting touches electronically to provide a count of said surgical articles comprising a ferrous metal.

10. The apparatus of claim 9 wherein said means for transmitting the touch electronically comprise a radio transmitter or an electronic cable.

11. An integrator-collector apparatus for use in operating room procedures wherein blood from a patient is absorbed by surgical sponges, said apparatus comprising, in combination:
    a) a means for counting surgical sponges which are prepared for use in an operating room procedure on said patient by the breaking of surgical sterile seals;
    b) a measuring means responsive to said means for counting for estimating the amount of blood absorbed by the surgical sponges actually used in with patient during said procedure;
    c) a measuring means for estimating blood removed by suction from with patient during said operating room procedure;
    d) a means for providing an estimate of incremental blood loss during said operating room procedure and for provides an estimate of the total blood loss at the termination of the procedure, said means for providing said estimates of blood loss being operatively associated with each of said measuring means defined in parts (b) and (c), above; and,
    e) in combination, means for providing an integrator function comprising a printing apparatus adapted to print on a paper strip, said printing apparatus being activated by impulses, said impulses causing printing of a count of surgical sponges, an estimate of blood absorbed in surgical sponges, an estimate of blood removed by suction, an estimate of incremental blood loss, and a count of surgical articles used during the procedure.

12. The apparatus of claim 11 wherein said impulses cause the printing of the date and time of every instrument, sponge, and needle used during the procedure.

13. The apparatus according to claim 12 further comprising means for corellating each material used in said operating room procedure with a billing price to said patient, and means for generating a record which can be used for billing purposes.

* * * * *